United States Patent
Zeichner et al.

(10) Patent No.: US 10,520,503 B2
(45) Date of Patent: Dec. 31, 2019

(54) COMPOSITIONS AND METHODS FOR DETERMINING THE LIKELIHOOD OF APPENDICITIS

(71) Applicants: Children's Research Institute, Children's National Medical Center, Washington, DC (US); University of Maryland, Baltimore, Baltimore, MD (US)

(72) Inventors: Steven L. Zeichner, Washington, DC (US); Anthony Sandler, Washington, DC (US); Claire Fraser, Baltimore, MD (US); Katherine Davenport, Washington, DC (US); Emmanuel Mongodin, Baltimore, MD (US); Hope Jackson, Washington, DC (US)

(73) Assignees: CHILDREN'S RESEARCH INSTITUTE, CHILDREN'S NATIONAL MEDICAL CENTER, Washington, DC (US); UNIVERSITY OF MARYLAND, BALTIMORE, Baltimore, MD (US)

( * ) Notice: Subject to any disclaimer, the term of this patent is extended or adjusted under 35 U.S.C. 154(b) by 647 days.

(21) Appl. No.: 14/618,695

(22) Filed: Feb. 10, 2015

(65) Prior Publication Data

US 2015/0225784 A1 Aug. 13, 2015

Related U.S. Application Data

(60) Provisional application No. 61/938,447, filed on Feb. 11, 2014.

(51) Int. Cl.
*C12Q 1/6883* (2018.01)
*C12Q 1/689* (2018.01)
*G01N 33/569* (2006.01)

(52) U.S. Cl.
CPC ....... *G01N 33/56911* (2013.01); *C12Q 1/689* (2013.01); *C12Q 1/6883* (2013.01); *G01N 2800/06* (2013.01)

(58) Field of Classification Search
None
See application file for complete search history.

(56) References Cited

U.S. PATENT DOCUMENTS

2009/0180987 A1* 7/2009 Stritzker ............... A61K 33/24
424/93.2

FOREIGN PATENT DOCUMENTS

WO 2012-170478 A2 12/2012

OTHER PUBLICATIONS

Ramasamy, D. et al. Standards in Genomic Sciences 8:336 (Jun. 2013).*

(Continued)

*Primary Examiner* — Diana B Johannsen
(74) *Attorney, Agent, or Firm* — Michael X. Ye; Morris, Manning & Martin, LLP

(57) ABSTRACT

A method for determining a likelihood of appendicitis in a subject is disclosed. The method comprises the steps of (a) determining the relative abundance of microorganisms corresponding to one or more operational taxonomic units (OTUs) in a test biological sample obtained from the subject; (b) comparing the relative abundance of the microorganisms in each of the one or more OTUs to a corresponding reference value assigned to each of the one or more OTUs, and (c) determining a likelihood of appendicitis in the subject based on the result in step (b), wherein a significant increase in relative abundance of the microorganisms in the one or more OTUs indicates a high risk of appendicitis in the subject. Also disclosed is a kit for determining a likelihood of appendicitis in a subject.

6 Claims, 2 Drawing Sheets

(56) References Cited

OTHER PUBLICATIONS

Swidsinski, A. et al. Saudi J. Gastroenterol. 18(1):55 (Jan.-Feb. 2012).*
Naoum, J.J. et al. The American Journal of Surgery 184:587 (2002).*
Lerner, A. et al. Antimicrobial Agents and Chemotherapy 57(3):1474 (Mar. 2013; online Jan. 7, 2013).*
Segata, N. et al. Genome Biology 13:R42 (2012).*
Schumacher, U.K. et al. 1997. Clinical Microbiology and Infection 3(1):134.*
Siqueira, J.F. et al. 2004. Journal of Endodontics 30(12):851 (abstract only).*
Guinane et al., "Microbial composition of human appendices from patients following appendectomy" MBio. 4(1), e00366-12 (internal pp. 1-6) (2013). See whole document.
Yang et al., "Intestinal microbiota composition of interleukin-10 deficient C57BL/6J mice and susceptibility to helicobacter hepaticus-induced colitis" PloS One, 8(8), e70783 (internal pp. 1-13) (2013). See whole document.
Kostic et al., "Genomic analysis identifies association of Fusobacterium with colorectal carcinoma" Genome Research, 22(2), pp. 292-298 (2012). See whole document.
Jackson et al., "Culture-independent evaluation of the appendix and rectum microbiomes in children with and without appendicitis" PloS One, 9(4), e95414 (internal pp. 1-9) (Apr. 2014). See whole document.
International Search Report and Written Opinion issued in Application No. PCT/US2015/015234 dated Apr. 24, 2015.

\* cited by examiner

COMPOSITIONS AND METHODS FOR DETERMINING THE LIKELIHOOD OF APPENDICITIS

This application claims priority to U.S. patent application Ser. No. 61/938,447, filed Feb. 11, 2014. The entirety of the aforementioned application is incorporated herein by reference.

FIELD

The present invention relates to non-invasive, non-imaging methods for determining the likelihood of appendicitis.

BACKGROUND

Appendicitis is a condition characterized by inflammation of the appendix. Cases typically require removal of the inflamed appendix, either by laparotomy or laparoscopy. Untreated, mortality is high, mainly because of peritonitis and shock.

Appendicitis is among many human diseases for which the diagnosis is complicated by the heterogeneity of its clinical presentation. Patients with many other disorders can present with symptoms similar to those of appendicitis. Examples include the following: pelvic inflammatory disease (PID) or tubo-ovarian abscess, endometriosis, ovarian cyst or torsion, ureterolithiasis and renal colic, degenerating uterine leiomyomata, diverticulitis, inflammatory bowel disease, colonic carcinoma, rectus sheath hematoma, cholecystitis, bacterial enteritis, viral gastroenteritis, mesenteric adenitis and omental torsion. It remains the most common surgical emergency of children, with initial diagnosis accuracy additionally challenged because of non-specific but similar symptoms of many other conditions. Delays in accurate diagnosis lead to increased mortality, morbidity and costs associated with the complications of appendicitis.

The use of high resolution computed tomography (CT) to identify appendiceal inflammation was hoped to improve both the diagnosis and treatment of appendicitis. Though variable, these improvements have been modest at best, with rates of unnecessary appendectomies and ruptures of 3-30% and 30-45%, respectively. In addition, availability of, and experience with, CT limit the usefulness of this approach. Furthermore, recently its use has been re-evaluated due to concerns of cancer risk due to radiation exposure. Ultrasonography is another imaging modality used to diagnose appendicitis, but ultrasonography requires a skilled operator, who may not be immediately available at night or on weekends, and the diagnostic accuracy of ultrasonography is limited.

Development of non-invasive diagnostics is therefore needed and desirable.

SUMMARY

One aspect of the present application relates to a method for determining a likelihood of appendicitis in a subject. The method comprises the steps of (a) determining the relative abundance of microorganisms corresponding to one or more operational taxonomic units (OTUs) in a test biological sample obtained from the subject; (b) comparing the relative abundance of the microorganisms in each of the one or more OTUs to a corresponding reference value assigned to each of the one or more OTUs, and (c) determining a likelihood of appendicitis in the subject based on the result in step (b), wherein a significant increase in relative abundance of the microorganisms in the one or more OTUs indicates a high risk of appendicitis in the subject.

In some embodiments, the subject is considered to have appendicitis if the test biological sample from the subject exhibits a significant increase in relative abundance of microorganisms in one or more OTUs compared to the corresponding reference value. In some embodiments, the OTU is defined by a bacterial genus. In certain particular embodiments, the method includes analysis of one or more OTUs selected from the group consisting of *Bulleidia*, *Porphyromonas* and *Dialister*. In other embodiments, the method includes analysis of one or more OTUs selected from the group consisting of *Bulleidia*, *Porphyromonas*, *Dialister*, *Parvimonas*, *Bilophilia*, *Mogibacterium*, *Aminobacterium*, *Proteus*, *Anaerovax*, *Anaerofilum*, *Prevotella* and *Fusibacterium*. In other embodiments, the method includes analysis of one or more OTUs selected from the group consisting of *Bulleidia*, *Porphyromonas*, *Dialister*, *Parvimonas*, *Bilophilia*, *Mogibacterium*, *Aminobacterium*, *Proteus*, *Anaerovax*, *Anaerofilum*, *Prevotella*, *Fusibacterium*, *Peptostreptococcus*, *Fusobacterium* and *Actinomycineae*.

In some embodiments the subject is considered to have appendicitis if the test biological sample exhibits a significant increase in the relative abundance of microorganisms for at least 2, 3, 4, 5 or 6 OTUs from the group consisting of *Bulleidia Porphyromonas*, *Dialister*, *Parvimonas*, *Bilophilia*, *Mogibacterium*, *Aminobacterium*, *Proteus*, *Anaerovax*, *Anaerofilum*, *Prevotella*, *Fusibacterium*, *Peptostreptococcus*, *Fusobacterium* and *Actinomycineae*.

In some embodiments, the test biological sample is collected from a rectal swab. In some embodiments, the test biological sample is a feces sample. In other embodiments, the test biological sample is a blood sample.

In some embodiments, the step of determining the relative abundance of microorganisms corresponding to a given OTU in each of steps (a) and (b) comprises hybridization of genomic DNAs from the test biological samples to nucleic acid probes specific for each OTU. In other embodiments, the step of determining the relative abundance of microorganisms corresponding to a given OTU in each of steps (a) and (b) is based on sequence analysis of polynucleotides amplified from genomic bacterial DNAs isolated from the test biological sample.

Polynucleotides may be amplified from one or more phylogenetically informative gene sequences specific for a given OTU. In one embodiment, the phylogenetically informative gene sequence is a rRNA gene sequence. In certain preferred embodiments, the phylogenetically informative gene sequence is a 16S rRNA gene sequence.

In another embodiment, the step of determining the relative abundance of microorganisms corresponding to an OTU in each of steps (a) and (b) is based on quantitative analysis of polypeptides in the test biological sample.

In certain embodiments, the method may further include the step of administering an antibiotic, surgically removing the subject's appendix, or both.

In another aspect, the present application provides an assay kit for determining a likelihood of appendicitis in a subject. In some embodiments, the kit includes detectors for two or more OTUs selected from the group consisting of *Bulleidia*, *Porphyromonas*, *Dialister*, *Parvimonas*, *Bilophilia*, *Mogibacterium*, *Aminobacterium*, *Proteus*, *Anaerovax*, *Anaerofilum*, *Prevotella*, *Fusibacterium*, *Peptostreptococcus*, *Fusobacterium* and *Actinomycineae*. In some embodiments, the assay kit comprises a plurality of probes and/or primers capable of detecting or amplifying polynucleotides specific for two or more OTUs, wherein the two or more OTUs comprise (1) two or more OTUs selected from the group consisting of *Bulleidia* Bullet, *Porphyromonas* and *Dialister*, or (2) one or more OTUs selected from the group consisting of *Bulleidia Porphyromonas* and *Dialister*, and one or more OTUs selected from the group consisting of *Parvimonas, Bilophilia, Mogibacterium, Aminobacterium, Proteus, Anaerovax, Anaerofilum, Prevotella, Fusibacterium, Peptostreptococcus, Fusobacterium* and *Actinomycineae*. In some embodiments, the kit further includes one or more reagents for purifying bacterial nucleic acids, at least one polymerase enzyme suitable for amplification of genomic DNA sequences, or both.

In certain embodiments, the plurality of probes and/or primers may include multiple pairs oligonucleotides, whereby each pair of oligonucleotides is suitable for amplifying a phylogenetically informative gene sequence specific for a particular OTU. The phylogenetically informative gene sequence may correspond to a rRNA gene, such as a 16S rRNA gene specific for a particular OTU.

In some embodiments, the kit may further include a computer readable storage medium containing software facilitating entry of nucleotide sequences obtained from a test biological samples and from one or more non-diseased control samples; comparative analysis of nucleotide sequences obtained from the test biological sample and the non-diseased control samples; statistical analysis of the relative abundance of nucleotide sequences obtained from the test biological sample and the non-diseased control samples, or a combination thereof.

BRIEF DESCRIPTION OF THE DRAWINGS

The accompanying drawings illustrate one or more embodiments of the application and, together with the written description, serve to explain the principles of the application.

FIG. 2 lists the taxa in each category; the numbers in parentheses for each heading lists the number of genera in that category.

DETAILED DESCRIPTION OF THE INVENTION

Figure 1:
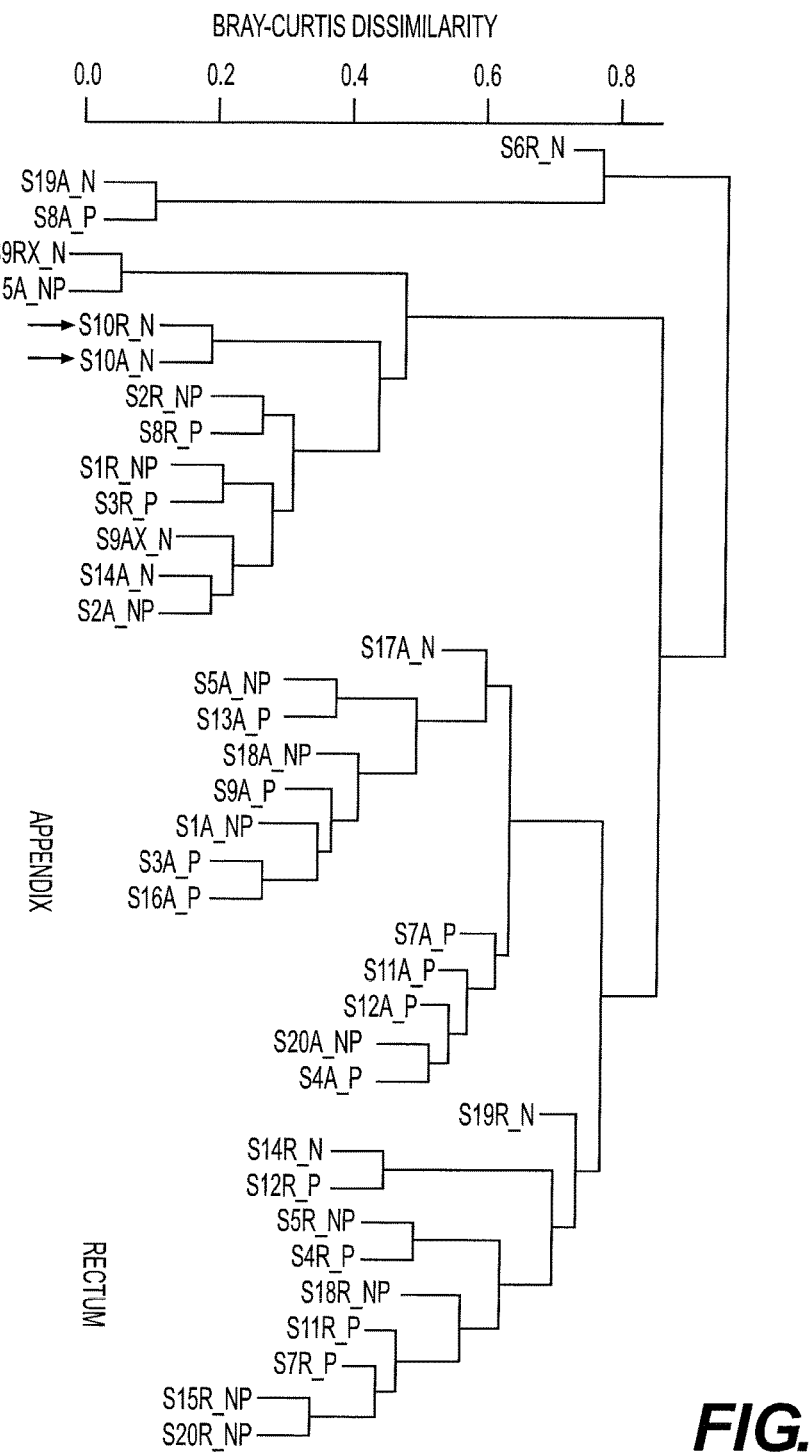
FIG. 1 shows a Bray-Curtis Cluster Dendogram illustrating similarities in microbial composition among rDNA profiles generated from appendix and rectum samples. This abundance-weighted measurement measures how similar two communities are in terms of their genus composition using the Bray-Curtis metric (Bray, J R et al., *Ecol. Monogr.* 27: 325-349, 1957; Field, J G et al., *Mar. Ecol. Prog. Ser.* 8: 37-52, 1982). 36 samples were analyzed (16 rectal samples and 20 appendix samples). 13 appendix samples clustered together. A group of 10 rectal samples clustered separately from the appendix samples, suggesting that the microbiome of the rectum differs from the microbiome of the appendix. Only one pair of rectal-appendix samples from the same subject (subject 10; black arrows) clustered together. The appendix cluster was composed almost entirely (12 out of 13 samples) of appendicitis samples, both non-perforated and perforated, suggesting that the appendix microbiome associated with appendicitis differs from the microbiome of the normal appendix. For the rectal sample cluster, 8 samples out of 10 samples from patients with appendicitis, both non-perforating and perforating, clustered together, suggesting that the microbiome of the rectum in patients with appendicitis is distinct from the microbiome of the rectum from patients without appendicitis. Samples are listed by ID number, SnX/Y, where n is the subject identification number, X describes the body site (A for appendix, R for rectum) and Y describes the patient's diagnosis (N for normal appendix, NP for an appendix with non-perforating appendicitis and P for an appendix with perforating appendicitis).

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. The present invention is not intended to be limited to the embodiments shown, but is to be accorded the widest possible scope consistent with the principles and features disclosed herein.

Unless defined otherwise, all technical and scientific terms used herein have the same meanings as commonly understood by one of skill in the art to which the disclosed method and compositions belong. It must be noted that as used herein and in the appended claims, the singular forms "a," "an," and "the" include plural reference unless the context clearly dictates otherwise. Thus, for example, reference to "a probe" includes a plurality of such probes; reference to "the probe" is a reference to one or more probes and equivalents thereof known to those skilled in the art and so forth.

Definitions

The term "microorganism" refers to an organism that is too small to be visible with the naked eye. Microorganisms include bacteria (Archaea, Eubacteria), yeast, fungi, and for the purposes of this disclosure, shall be understood to include viruses. The term "species of microorganism" is used herein to refer to a taxonomically and/or genetically distinct group of microorganism.

The term "microbiota" or "microflora" refers to an assemblage of microorganisms localized to a distinct environment. For example, a "rectal microbiota" is an assemblage of one or more species of microorganisms that are localized to, or found in, the rectum. In this case, a "normal rectal microbiota" corresponds to a population of microorganisms localized to the rectum in a normal, that is, a non-pathological or non-pathogenic state with no sign or symptom corresponding to or resulting from a pathology of the rectum.

The term "microbial community" refers to one or more microbial populations found together in a shared environment. For example, a shared environment can be a defined site or location on or in a subject (e.g., a host), or can be an environmental site or location not associated with a subject. Thus, a shared environment can be a specific organ or tissue within the body of a subject, such as the rectum or appendix, etc.

A "microbial profile" refers to a representative collection of species, genus groups, and/or other taxonomic groups present in a sample taken from a microbial community.

As used herein the term "genus" is used with reference to a principal rank in the taxonomic hierarchy, falling below the family level and above the species level; "species" is used is used with reference to a fundamental rank in the taxonomic hierarchy falling below the genus level.

The term "biomarker" refers to any molecule that differs between species, strains, or OTUs and for which the difference can be detected. Most typically, a biomarker is polymorphic nucleic acid, or a polymorphic polypeptide encoded by a polymorphic nucleic acid. The term "polymorphic" or "polymorphism" refers to a nucleic acid or polypeptide that exists in two or more variant forms. The variant forms may be detectable at the molecular level (e.g., at the nucleic acid, polypeptide, lipid or polyssacharide level) or may be detectable as functional variants, for example, by phenotypic differences between species or strains. In some cases, a biomarker is not directly encoded by a polymorphic polynucleotide. For example, polymorphic glycoproteins can be detected based on differences in their carbohydrate moieties. In addition, in some cases the can be a metabolic product that differs between species, for example a detectable metabolite, such as a secondary metabolite, that differs between species. In some embodiments, the term "biomarker" also refers to a metabolite profile that differs between species, strains or OTUs. A biomarker that differs between OTUs may be refered to as OTU markers.

The biomarker may include a "phylogenetically informative gene," that is, a functional genetic element that differs between species. A phylogenetically informative gene is one comprising polymorphic nucleic acid sequence differences reflecting the evolutionary relationships between different microorganisms. These polymorphic sequences can be detected by aligned related nucleic acid sequences across a window of comparison. Such differences can be identified by nucleic acid sequencing of the polymorphic sequences using well known methods, including automated nucleic acid sequencing methods. Alternatively, polymorphic nucleotide sequence differences can be detected by a variety of techniques including analysis of restriction fragment length polymorphisms (RFLPs), amplified fragment length polymorphisms (AFLPs), allele specific hybridization (ASH), single nucleotide polymorphism (SNP), single-strand conformation polymorphisms (SSCP) etc.

A "rRNA gene" is an exemplary biomarker for microbes. rRNA genes encode the ribonucleic acid ("RNA") components of ribosomes, and can be categorized based on the size of the ribosomal component in which the encoded RNA is localized. Prokaryotic rRNA genes include: the 16S rRNA gene, the 23S rRNA gene and the 5S rRNA gene.

As used herein, the term "rDNA profile" refers to a collection of specific DNA sequences amplified from a sample, whereby the DNA sequences code for any of a wide variety of different bacterial rRNA genes.

As used herein, the term "taxonomic unit" is a group of organisms that are considered similar enough to be treated as a separate unit. A taxonomic unit may comprise a family, genus, species or population within a species (e.g., strain), but is not limited as such.

As used herein the term "operational taxonomic unit" (OTU) refers to a group of microorganisms considered similar enough to be treated as a separate unit. An OTU may comprise a taxonomic family, genus or species but is not limited as such. In certain cases, the OTU may include a group of microorganisms treated as a unit based on e.g., a sequence identity of ≥95%, ≥90%, ≥80%, or ≥70% among at least a portion of a differentiating biomarker, such as the 16S rRNA gene.

As used herein, the term "relative abundance" relates to the abundance of microorganisms of a particular OTU in a test biological sample compared to the abundance of microorganisms of the corresponding OTU in one or more non-diseased control samples. The "relative abundance" may be reflected in e.g., the number of isolated species corresponding to an OTU or the degree to which a biomarker specific for the OTU is present or expressed in a given sample. The relative abundance of a particular OTU in a sample can be determined using culture-based methods or non-culture-based methods well known in the art. Non-culture based methods include sequence analysis of amplified polynucleotides specific for an OTU or a comparison of proteomics-based profiles in a sample reflecting the number and degree of polypeptide-based, lipid-based, polyssacharide-based or carbohydrate-based biomarkers characteristic of one or more OTUs present in the samples. Relative abundance or abundance of a taxa or OUT can be calculated with reference to all taxa/OTU detected, or with reference to some set of invariant taxa/OTUs.

As used herein, the term "significantly altered relative abundance" refers to a statistically significant increase or reduction in the relative abundance of the number of microorganisms of a particular OTU compared to the total microorganisms in the sample or to the number of microorganisms of the corresponding OTU present in another sample. In some embodiments, a "significant increase" or "significant reduction" in relative abundance is defined as a statistically significant increase or statistically significant reduction over a reference value. In some embodiments, a statistically significant increase or statistically significant reduction is an increase or a reduction that is twice, three-times or four-times of the standard deviation of the relative abundance. In some embodiments, a statistically significant increase or statistically significant reduction is an increase or a reduction with a P-value equal to, or smaller than, 0.1, 0.05, 0.01 or 0.005.

In some embodiments, "significant reduction" or "significant increase" in relative abundance means a statistically significant difference in one or more indicator species compared with each other or with reference species using a non-parametric statistical test, such as a signed-rank test. In some embodiments, a "significant reduction" or "significant increase" in relative abundance are determined using models that employ Bayesian inference and related approaches. In some embodiments, the microbiomic data is combined with clinical metadata to produce a composite appendicitis likelihood score using a Bayesian model. For example, finding *Bulleidia* in the rectum without anything else might not be significant, but finding *Bulleidia* in the rectum of a patient with fever and abdominal pain might be highly significant.

In certain embodiment, an increase in relative abundance reflects an increase of 10%, 20%, 30%, 40%, 50%, 60%, 70%, 80%, 90%, 100% or more over a reference value. In other embodiment, an increase in relative abundance reflects a 2-fold, 3-fold, 5-fold, 10-fold, 20-fold, 50-fold or 100-fold increases over a reference value.

As used herein, the term "a high risk of appendicitis" refers to a risk level of appendicitis or likelihood of appendicitis that requires further investigation or clinical test, such as CT scan or ultrasonography.

Method for Diagnosing Appendicitis

One aspect of the present application relates to a method for diagnosing appendicitis in a subject. The method comprises the steps of: (a) determining the relative abundance of microorganisms corresponding to one or more operational taxonomic units (OTUs) in a test biological sample obtained from the subject; (b) comparing the relative abundance of the microorganisms in each of the one or more OTUs to a corresponding reference value assigned to each of the one or more OTUs, based on the relative abundance of microorganisms in each of the one or more corresponding OTUs in one or more non-diseased control samples, and (c) determining whether the subject has appendicitis based on the comparison in step (b).

In some embodiments, the subject is considered to have appendicitis if the test biological sample exhibits an increase in relative abundance of microorganisms in one or more OTUs.

In some embodiments, the OTU is defined by a bacterial genus. In certain particular embodiments, the method includes analysis of one or more OTUs selected from the group consisting of *Bulleidia*, *Porphyromonas* and *Dialister*, In other embodiments, the method includes analysis of one or more OTUs selected from the group consisting of *Bulleidia Bullcdia*, *Porphyromonas*, *Dialister*, *Parvimonas*, *Bilophilia*, *Mogibacterium*, *Aminobacterium*, *Proteus*, *Anaerovax*, *Anaerofilum*, *Prevotella* and *Fusibacterium*. In other embodiments, the method includes analysis of one or more OTUs selected from the group consisting of *Bulleidia*, *Porphyromonas*, *Dialister*, *Parvimonas*, *Bilophilia*, *Mogibacterium*, *Aminobacterium*, *Proteus*, *Anaerovax*, *Anaerofilum*, *Prevotella*, *Fusibacterium*, *Peptostreptococcus*, *Fusobacterium* and *Actinomycineae*.

In some embodiments, the test biological sample is a feces sample. In other embodiment, the test biological sample is collected from a rectal swab. In other embodiments, the test biological sample is a blood sample.

In some embodiments, the reference value is derived from non-diseased biological sample(s). In some embodiment, the reference value is derived from a plurality of biological samples, such as feces samples, rectal swab samples, or blood samples, collected from non-diseased individuals.

Determination of the Relative Abundance of Microorganisms in a Biological Sample The relative abundance of microorganisms in the biological sample can be determined using culture-based methods and culture-independent methods. In some embodiments, the relative abundance of microorganisms in the biological sample is determined by a culture-independent method. Several culture-independent approaches are useful for analyzing large numbers of samples and offer the possibility of being able to detect statistically significant differences between normal communities and those associated with diseases. Culture-independent methods offer significant advantages over culture-based methods for classifying microorganisms that require culture prior to analysis. For example, culture-independent methods decrease labor and materials costs by eliminating the requirement that colonies of microorganisms be established prior to analysis. More importantly, by eliminating the need for culturing of microorganisms prior to analysis, bias due to preferential growth under various culture conditions is eliminated. By eliminating this bias, it becomes possible to comprehensively determine the variety of microbiota that inhabit an environment under normal and perturbed conditions.

Culture-independent methods for identifying the constituent species in a sample of microorganisms involve detecting or identifying biomarkers specific for one or more OTUs. A biomarker can be any molecular species present in or produced by the microorganism, so long as it can be detected directly or indirectly. Preferably, the molecular species exists in sufficiently polymorphic forms that it can alone, or in combination with other molecular species, be used to determine the identity of the microorganism from which it is obtained. In certain embodiments, the biomarker can be a protein, lipid or polyssachride species that differs in a predictable way between species, genus or OTUs. For example, the biomarker can be an antigen that differs between species or genus of microorganism and can be distinguished, e.g., by the binding of an antibody, chromatographic signature, mass spectroscopy signature or other specific chemical reaction.

In some embodiments, the culture-independent methods involve detection or identification of one or more the biomarkers or phylogenetically informative genes. Phylogenetically informative genes may include polymorphic polynucleotide sequences present in genomic sequences, such as protein coding regions, non-coding regions, catalytic RNA sequences (e.g., 16S rRNAs) and the like. Phylogenetically informative genes (e.g., homologs or orthologs of a gene) may be shared by a given OTU, reflecting their origin from a common ancestor. However, they may differ between species outside of the OTU. The polynucleotide sequences of orthologous genes in different species have diverged over time accumulating mutations (e.g., insertions, deletions, point mutations, and/or recombination events), which can be detected using any of a variety of methods for detecting sequence differences. Typically, a phylogenetically informative gene is one for which at least one ortholog can be detected among a large number of species of microorganisms.

In some embodiments, the step of determining the relative abundance of microorganisms corresponding to a given OTU comprises hybridization of genomic DNAs from the test biological samples to nucleic acid probes specific for each OTU. In other embodiments, the step of determining the relative abundance of microorganisms corresponding to a given OTU is based on sequence analysis of polynucleotides amplified from genomic bacterial DNAs isolated from the test biological sample. In this case, polynucleotides containing phylogenetically informative gene sequences specific for a given OTU are amplified from nucleic acids isolated from a sample. Nucleic acids for amplification may include DNA, RNA, or both, and can be prepared by any methods known in the art for the isolation and purification of nucleic acids.

In other embodiments, the step of determining the relative abundance of microorganisms corresponding to an OTU is based on analysis of polypeptide differences between the test biological sample and the one or more non-diseased biological samples.

In certain embodiments, profiles of microbial communities are generated from a test sample based on the collection of biomarkers or phylogenetically informative gene sequence sequences present in a sample. In one embodiment, the biomarkers or phylogenetically informative gene sequences include one or more rRNA gene sequences (e.g. 16S, 23S, 5S rRNAs) specific for a given OTU. In certain preferred embodiments, 16S rRNA profiles of microbial communities are generated. The 16S rRNA gene is particularly suitable as a biomarker for the identification and phylogenetic analysis of microorganisms. The 16S rRNA gene offers several significant advantages as a biomarker. For example, some regions of the 16S rRNA gene are highly conserved and universal PCR primer sets exist that can amplify the 16S rRNA gene from the overwhelming majority of bacteria and Archea, respectively. The 16S rRNA gene also includes regions that are less well conserved making it possible to identify taxons. Additionally, the 16S rRNA gene is believed to have changed at a fairly constant rate during evolution, making it, in effect, an evolutionary clock with each nucleotide difference translating to an evolutionary time unit. The approximately 1500 bp sequence of the 16S rRNA gene contains enough information to predict the identity and phylogeny of an organism with high precision. Furthermore, an extensive, rapidly growing database exists for this gene. For example, the ARB database (available on the world wide web at arb-home.de) contains over 25,000 aligned 16S rRNA gene sequences. Additional databases include that of the Ribosomal Database Project (Cole et al., *Nucl. Acids. Res.* 31:442-443, 2003) and the NCBI database (available on the world wide web at ncbi.nlm.nih.gov/entrez).

Biomarkers, including phylogenetically informative genes, such as rRNA genes, may be amplified from total community DNA in a PCR and the amplicons are sequenced using any one of several commercially available "high throughput" or "next generation" sequencing systems, such as the Illumina MiSeq or HiSeq platforms, the 454 pyrosequencing system, or the Ion Torrent system.

Additional examples of phylogenetically informative genes suitable as biomarkers include: rpoB; gyrB; gyrA; tmRNA; recA; EF-Tu (tuf); groEL (cnp60, hsp60); atpD; ompA gene; gapA; pgi; fusA; ileS; lepA; leuS; pyrG; recG; rplB. Other genes (for example functional genes encoding related enzymes that perform a defined function) also can be utilized, at least with respect to narrower groups of microorganisms. Examples of such functional genes include the pmoA/amoA genes; the mmoX gene; the nifH gene; the nirS gene; the nirK gene; the norB gene; the mcrA gene; and the rbcL gene. A person of ordinary skill will appreciate that any polymorphic gene, gene family or molecule specifically associated with a particular taxa or OTU can be utilized as a biomarker.

Procedures for detecting and/or enumerated species within a given OTU can also be based on the physical properties of the nucleic acids. For example, polymorphic polynucleotides can be distinguished based on hybridization to a probe nucleic acid and/or PCR-based amplification thereafter. Hybridization can be performed with the probe and target nucleic acids in solution, for example, followed by capture of the duplexed nucleic acid. More commonly polymorphic polynucleotides are detected by hybridization methods in which the probe or the target nucleic acids is attached to a solid phase, such as a membrane, a "chip" (for example, a glass or plastic microarray) or a column or other substrate. For example, the target polymorphic polynucleotide can be detected by hybridization of a labeled DNA (or even an RNA) probe. Similarly, the target polymorphic polynucleotide can be DNA, e.g., genomic DNA, cDNA or amplification products, or RNA, or a protein capable of specifically binding to a distinct DNA sequence.

Hybridization of nucleic acids is dependent on a variety of parameters, including for example, the length, degree of complementarity, nucleotide sequence composition (e.g., GC v. AT content), and nucleic acid type (e.g., RNA versus DNA). In general, the more similar the sequences of the two nucleic acids are, the more stringent the conditions at which they will hybridize. The stringency of hybridization conditions are sequence-dependent and are different under different environmental conditions. Thus, hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found, for example, in Sambrook et al., Molecular Cloning: A Laboratory Manual, Cold Spring Harbor Laboratory Press, Cold Spring Harbor, N.Y. (2001) and Ausubel et al., Short Protocols in Molecular Biology, 4$^{th}$ ed., John Wiley & Sons, Inc. (1999).

For purposes of the present disclosure, "stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize. In contrast nucleic acids that hybridize under "low stringency conditions include those with much less sequence identity, or with sequence identity over only short subsequences of the nucleic acid.

Methods for detecting the polymorphic polynucleotide sequences may involve analysis of restriction fragment length polymorphisms (RFLPs), terminal restriction fragment polymorphisms (T-RFLPs), amplified fragment length polymorphisms (AFLPs), single nucleotide polymorphisms (SNPs), single-strand conformation polymorphisms (SSCPs), simple sequence repeat (SSRs), randomly amplified polymorphic DNA (RAPD) and/or variable sequence amplification. These methods may alternatively, or additionally, include allele specific hybridization (ASH), self-sustained sequence replication, helicase-dependent isothermal DNA amplification, loop-mediated isothermal amplification (LAMP), strand displacement amplification (SDA), nicking enzyme amplification reaction (NEAR), rolling circle amplification and/or recombinase polymerase amplification.

Amplification products can be produced using a variety of well-known protocols. An example of amplification is the polymerase chain reaction (PCR), in which a biological sample collected from a subject is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. Numerous procedures for PCR are known in the art and exemplary protocols can be found, e.g., in Sambrook and Ausubel (supra). Products of amplification can be characterized by electrophoresis, restriction endonuclease cleavage patterns, oligonucleotide hybridization or ligation, and/or nucleic acid sequencing using standard techniques. Other examples of amplification include isothermal techniques that do not require thermocyclers. Examples of sequence-specific isothermal DNA amplification technologies include, but are not limited to, loop-mediated isothermal amplification (LAMP), strand displacement amplification (SDA), helicase-dependent amplification (HDA) and nicking enzyme amplification reaction (NEAR).

LAMP uses 4-6 primers recognizing 6-8 distinct regions of target DNA. A strand-displacing DNA polymerase initiates synthesis and 2 of the primers form loop structures to facilitate subsequent rounds of amplification. LAMP is rapid, sensitive, and amplification is so extensive that the magnesium pyrophosphate produced during the reaction can be seen by eye, making LAMP well-suited for field diagnostics.

SDA relies on a strand-displacing DNA polymerase, typically Bst DNA Polymerase, Large Fragment or Klenow Fragment (3'-5' exo-), to initiate at nicks created by a strand-limited restriction endonuclease or nicking enzyme at a site contained in a primer. The nicking site is regenerated with each polymerase displacement step, resulting in exponential amplification. SDA is typically used in clinical diagnostics.

HDA employs the double-stranded DNA unwinding activity of a helicase to separate strands, enabling primer annealing and extension by a strand-displacing DNA polymerase. Like PCR, this system requires only two primers. HDA has been employed in several diagnostic devices and FDA-approved tests.

NEAR employs a strand-displacing DNA polymerase initiating at a nick created by a nicking enzyme, rapidly producing many short nucleic acids from the target sequence. This process is extremely rapid and sensitive, enabling detection of small target amounts in minutes. NEAR is commonly used for pathogen detection in clinical and biosafety applications.

Other amplification techniques include transcription-free isothermal amplification, as disclosed in U.S. Pat. No. 6,033,881, repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134. All the references described above are incorporated by reference herein.

In some embodiments, the amplification methods include methods for amplifying target polymorphic polynucleotides using universal primers that recognize a conserved sequence common between species, which flank a polymorphic region suitable as a biomarker. Alternatively, amplification can be performed using sequence specific or selective primers that hybridize to and selectively amplify only one (or a subset) of target polymorphic polynucleotides. Optionally, a quantitative amplification (quantitative PCR method can be utilized). Frequently, amplification products can be directly detected (that is detected without the need to hybridize a labeled probe). For example, amplification products are commonly produced from nucleic acids derived from samples of microorganisms in sufficient quantity that they can be visualized directly, for example, following size separation by electrophoresis on an agarose or acrylamide gel. Optionally, the amplification products can be treated with a restriction enzyme, e.g., as described above with respect to detection of T-RFLPs.

Alternatively, a biomarker can be detected in situ in a sample of microorganism, without isolating or otherwise preparing a nucleic acid from the sample of microorganism. For example, amplification methods can be adapted to in situ procedures, in which the biomarker is amplified while still located in the cell of the microorganism, e.g., utilizing labeled primers that result in a product detectable optically, enzymatically, chemically or autoradiographically.

In some embodiments, genomic DNA is isolated from the biological sample and is evaluated for the microbial profile/diversity and relative abundance/richness of certain marker microorganisms in the biological sample. In one embodiment, a rDNA profile of amplified rDNA sequences (corresponding to rRNA genes) is assembled by PCR amplification or other amplification methods using oligonucleotide primers targeting bacterial rRNA genes, such as the 16S, 23S and 5S rRNA genes. The oligonucleotide primers may contain specific sequences targeting a specific species or operational taxonomic unit (OTU) or they may be degenerate oligonucleotides capable of hybridizing to a variety of different rDNA regions conserved in a given family or genus. The amplified sequences may be analyzed directly by nucleotide sequence analysis. Alternatively, the amplified sequences may be used as a hybridization probe against a solid support comprising a plurality of well-defined probe sequences representing a plurality of different family, genus, species or OTU members, whereby the level of hybridization to a given probe is indicative of the abundance of particular bacterial family, genus, species or OTU member.

In some embodiments, the amplification-based assay utilizes a plurality of different oligonucleotide primer pairs, each primer pair targeting a given family, genus, species or OTU member for amplification of one or more rDNA regions so as to generate a rDNA profile. As an example, the oligonucleotides primers may contain specific sequences targeting a specific bacterial species or they may be degenerate oligonucleotides capable of hybridizing to a plurality of different rDNA regions corresponding to multiple species within a genus.

In certain embodiments, the oligonucleotide or oligonucleotide primer may contain a nucleic acid sequence specific to a single OTU in a bacterial genus, wherein the oligonucleotide constitutes a potential indicator for the presence of one more bacterial species corresponding to a given bacterial genus.

The level of microbial diversity or richness may be determined using any suitable diversity and richness method, including observed number of OTUs, Chao1 (richness), ACE (richness) (Chao & Bunge, *Biometrics* 58: 531-539, 2002), rarefaction, Shannon (diversity) and Simpson (diversity). These methods may be used to derive a numerical measure or estimator of diversity or richness, or coefficient in this case. A distance matrix of samples may be calculated using the Jaccard Index or Bray-Curtis index. Each of these two indices accounts the presence/absence/abundance of OTUs and characterizes the dissimilarity in microbial community membership. These and/or other measures of community diversity or richness can then be used in a population of subjects to compare test subjects who may have appendicitis with others that do not. The Jensen-Shannon divergence may also be calculated as a measure to determine how far the microbial community of a disease state lies from another (normal) state.

In other embodiments, the presence/absence/relative abundance relative abundance of OTUs are determined by detection of non-nucleic acid OTU markers such as taxa-specific proteins, taxa-specific polysaccharides, or taxa-specific lipids. In some embodiments, the non-nucleic OUT markers are detected by an antibody-based detection method such as ELISA or a dipstick test.

In some embodiments, the presence/absence/relative abundance relative abundance of one or more reference OTUs are also determined with methods described above. In some embodiments, the reference OTUs are OTUs that are known to be present in patient with normal appendix. In other embodiments, the reference OTUs are OTUs that are known to be present in the rectum of patients with or without appendicitis. In some embodiments, the reference OTUs are selected from the group consisting of *Fusobacterium, Peptostreptococcus, Frankineae, Dyadobacter, Curvibacter, Melissococcus, Variovorax,* and *Larkinella.*

Comparing the Relative Abundance of the one or more Marker Microorganisms and Determining a Likelihood of Appendicitis in the Subject The relative abundance of the one or more marker microorganisms in a biological sample from a subject compared to a reference number or range to determine the likelihood of appendicitis in the subject.

In some embodiments, the marker microorganisms include species directed to, but not limited to the genus groups, *Bulleidia, Porphyromonas, Dialister, Parvimonas, Bilophilia, Mogibacterium, Aminobacterium, Proteus, Anaerovax, Anaerofilum, Prevotella, Fusibacterium, Peptostreptococcus, Fusobacterium* and *Actinomycineae.*

In some embodiments, the relative abundance of *Bulleidia, Porphyromonas, Dialister* or a combination thereof is evaluated. A significant increase in the relative abundance of one or more of these bacterial genus groups is an indication of appendicitis. In some embodiments, a significant increase in the relative abundance in one of these genus groups is an indication of appendicitis. In other embodiments, a significant increase in the relative abundance in two of these genus groups is an indication of appendicitis. In yet other embodiments, a significant increase in the relative abundance in all three of these genus groups is an indication of appendicitis.

In some embodiments, a significant increase in relative abundance refers to a statistically significant increase in relative abundance with a P-value smaller than 0.5, 0.05, 0.03, 0.01 or 0.005 comparing to a reference relative abundance value. In some embodiments a statistically significant increase in abundance refers to other non-parametric statistical techniques or Bayesian statistics. In other embodiments, a significant increase in relative abundance refers to an increase in relative abundance that is at least 2-fold, 3-fold, 4-fold, 5-fold or 10-fold of the standard deviation of the original relative abundance comparing to a reference relative abundance value.

In certain embodiment, an increase in relative abundance reflects an increase of 10%, 20%, 30%, 40%, 50%, 60%, 70%, 80%, 90%, 100% or more over a reference value. In other embodiment, an increase in relative abundance reflects a 2-fold, 3-fold, 5-fold, 10-fold, 20-fold, 50-fold or 100-fold increases over a reference value.

In some embodiments, the reference relative abundance of a microorganism value is the average relative abundance or the range of relative abundance of the microorganism in the same type of sample in a reference population. The reference population may be a collection of subjects who do not have appendicitis. The reference population may be further selected based on age, sex, race, geographic distribution, and combinations thereof. The reference population of microorganisms may be further selected or adjusted based on the composition of the other organisms present in the gastrointestinal tract of the subject.

The determination of the likelihood of appendicitis in the subject may rely on a combination of the relative abundance of the marker microorganism and the symptom(s) of appendicitis in the subject. Examples of the symptoms of appendicitis include, but are not limited to; abdominal pain or tenderness, nausea, vomiting, loss of appetite, fever, constipation, inability to pass gas, diarrhea and abdominal swelling, and laboratory measurements including vital signs, such as temperature, respiratory rate, heart rate, blood pressure, hemoglobin oxygen saturation, white blood cell count and differential, neutrophil count, acute phase reactants, markers of inflammation, such as erythrocyte sedimentation rate or c-reactive protein, and combinations thereof. As used herein, the term "fever" is defined as a body temperature that is above normal. Generally, a patient is considered to have a fever if the body temperature is at or above 38° C. rectally, 37.5° C. orally, or 37.2° C. under armpit.

In some embodiments, a diagnosis of appendicitis is made if the subject has a significant increase in the relative abundance in any one of *Bulleidia, Porphyromonas* and *Dialister* in a rectal swab sample, fecal sample or blood sample, and exhibits at least one of the symptoms of appendicitis. In other embodiments, a diagnosis of appendicitis is made if the subject has a significant increase in the relative abundance in any two of *Bulleidia, Porphyromonas* and *Dialister* in a rectal swab sample, feces sample or blood sample, and exhibits at least one of the symptoms of appendicitis. In other embodiments, a diagnosis of appendicitis is made if the subject has a significant increase in the relative abundance in all three of *Bulleidia, Porphyromonas* and *Dialister* in a rectal swab sample, feces sample or blood sample, and exhibits at least one of the symptoms of appendicitis.

In some embodiments, the likelihood of appendicitis is determined by combining the data of the relative abundances of the microorganisms in the sample with additional clinical and laboratory data, such as (but not limited to) symptoms, signs (such as abdominal pain), temperature, white blood cell count, to produce a statistical model (e.g., frequentist inference, Bayesian, and other statistical models, including models obtained through machine learning approaches) for an appendicitis diagnosis.

In other embodiments, a diagnosis of appendicitis is made if the subject has a significant increase in the relative abundance of one or more of *Bulleidia, Porphyromonas* and *Dialister*, and a significant change in relative abundance of another marker microorganism in a rectal swab, feces sample or blood sample, with or without at least one symptom of appendicitis.

In some embodiments, the method of diagnosis further includes the step of administering an antibiotic, surgically removing the subject's appendix, or both. In other embodiments, the method of the present application may alternatively include or additionally include the step of confirming a preliminary diagnosis of appendicitis with a secondary diagnosis modality technology. Examples of secondary diagnosis modalities include, but are not limited to, CT scan and/or ultrasound.

Kits for Detection of Appendicitis

In another aspect, the present application provides an assay kit for diagnosing appendicitis. The kit may include a plurality of probes capable of detecting or amplifying nucleic acids specific for any of the OTUs or microbial genus groups described herein. In some embodiments, the kit includes one or more of probes and/or primers capable of detecting or amplifying polynucleotides specific for at least 1, 2 or 3 OTUs selected from the group consisting of *Bulleidia* Bullcdia, *Porphyromonas* and *Dialister*. In other embodiments, the kit further includes one or more of probes and/or primers capable of detecting or amplifying polynucleotides specific for at least 1, 2 or 3 OTUs selected from the group consisting of *Parvimonas, Bilophilia, Mogibac-* terium, *Aminobacterium, Proteus, Anaerovax, Anaerofilum, Prevotella, Fusibacterium, Peptostreptococcus, Fusobacterium* and *Actinomycineae*.

In another embodiment, the kit includes a plurality of probes capable of detecting or amplifying polynucleotides specific for at least 2, 3, 4, 5 or 6 OTUs selected from the group consisting of *Bulleidia, Porphyromonas, Dialister, Peptostreptococcus, Bilophila, Parvimonas, Mogibacterium, Fusobacterium, Aminobacterium, Proteus, Actinomycineae, Anaerovorax, Paenibacillaceae* I, *Acidobacteriaceae* GP4, *Pseudocardineae, Bergeyella* and *Rhizobium*.

In addition, the kit may further include one or more reagents for purifying bacterial nucleic acids, at least one polymerase enzyme suitable for amplification of genomic DNA sequences, or both.

In certain embodiments, the plurality of probes may include multiple pairs oligonucleotides, whereby each pair of oligonucleotides is suitable for amplifying a phylogenetically informative gene sequence specific for a particular OTU. The phylogenetically informative gene sequence may correspond to a rRNA gene, such as a 16S rRNA gene specific for a particular OTU.

In some embodiments, the kit further comprises detectors for one or more reference OTUs. In some embodiments, the reference OTUs are OTUs that are known to be present in the rectum of patients with or without appendicitis. In some embodiments, the reference OTUs are selected from the group consisting of *Fusobacterium, Peptostreptococcus, Frankineae, Dyadobacter, Curvibacter, Melissococcus, Variovorax, Larkinella, Escherichia, Enterococcus, Streptococcus, Lactobacillus, Staphylococcus, Proteus, Bacterioides, Bifidobacterium, Corynebacterium, Fusobacterium, Selenomonas, Paenibacillaceae, Acidobacgeriaceae, Pseudocardineae, Bergeyell* and *Rhizobium*.

In addition, the kit may further include a tangible computer readable storage medium containing software facilitating entry of nucleotide sequences obtained from one or more test biological samples; comparative analysis of nucleotide sequences obtained from the test biological sample and the corresponding reference values; statistical analysis of the relative abundance of nucleotide sequences obtained from the test biological samples; statistical analysis of the microbial biomarker data combined with an analysis of the clinical metadata or other laboratory data. In some embodiments, the tangible computer readable storage medium contains software or algorithms to make taxa/OTU comparisons, and taxa/OUT comparisons along with an analysis of the clinical metadata. As used herein, the term "clinical metadata" or "clinical indications" refers to clinical symptoms such as abdominal pain or tenderness, nausea, vomiting, loss of appetite, fever, constipation, inability to pass gas, diarrhea and abdominal swelling; vital body signs, such as body temperature, respiratory rate, heart rate, blood pressure, hemoglobin oxygen saturation; and laboratory data, such as white blood cell count and differential, neutrophil count, acute phase reactants, and markers of inflammation, such as erythrocyte sedimentation rate or c-reactive protein.

The present invention is further illustrated by the following examples that should not be construed as limiting. The contents of all references, patents and published patent applications cited throughout this application, as well as the Figures and Tables, are incorporated herein by reference.

Example

To investigate the role of microbiota in appendicitis, a pilot, culture-independent 16S rRNA-based study of microbiota of paired appendix and rectal samples was performed. Matched appendix and rectal swabs were collected from 21 children (age range: 5 months-18 years) undergoing an appendectomy, six with normal appendices and fifteen patients with appendicitis, nine of which were perforated. A total of 42 samples were processed and DNA extracted. After genomic DNA isolation, 16S rRNA genes were PCR amplified using the 27F and 338R broad-range bacterial primers and the PCR amplicons were sequenced using 454 Titanium pyrosequencing. Out of these 42 samples, 5 samples did not yield enough PCR amplicons and were subsequently removed from the analysis. From the remaining 37 samples that were successfully PCR-amplified and sequenced, a total of 325,342 non-chimeric sequences (8,793±3888 reads on average per sample) were obtained, which were assigned to a total of 13,751 unique operational taxonomic units (OTUs) using a cutoff of 95% sequence identity. The CloVR-16S v. 1.1 (http://clovr.org/methods/clovr-16s/) automated analysis pipeline was used to process the raw 454 pyrosequencing reads, perform taxonomic assignments and calculate microbial diversity and richness indices.

Microorganisms differing in relative abundance were identified using ANOVA ($p<0.05$) and characterized by anatomic location (appendix vs. rectum), disease state (appendicitis vs. normal) and disease severity (perforated vs. non-perforated). Median values of bacterial community richness and diversity calculated for samples groups are displayed in Table 1.

TABLE 1

Diversity and Richness Estimators (median values).

|  | N | Observed Number of OTUs (sobs calculator) | Chao1 (Richness) | ACE (Richness) | Shannon (Diversity) | Simpson (Diversity) |
| --- | --- | --- | --- | --- | --- | --- |
| Appendix | 20 | 237 | 507.621 | 911.130 | 2.742 | 0.150 |
| Rectal | 17 | 446 | 957.621 | 1371.363 | 3.534 | 0.083 |
| Appendix: Normal | 5 | 237 | 463.622 | 804.885 | 2.742 | 0.150 |
| Appendix: Non Perforated Appendicitis | 6 | 228 | 542.096 | 921.922 | 2.557 | 0.178 |
| Appendix: Perforated Appendicitis | 9 | 344 | 750.978 | 1241.873 | 3.041 | 0.100 |
| Rectal: Normal Appendix | 5 | 220 | 373.867 | 604.679 | 2.312 | 0.206 |
| Rectal: Non Perforated Appendicitis | 6 | 411 | 884.560 | 1363.194 | 3.779 | 0.056 |
| Rectal: Perforated Appendicitis | 6 | 478 | 1101.720 | 1680.009 | 3.756 | 0.078 |

The observed number of OTUs (sobs calculator in mothur) was the highest for the rectal samples, compared to appendix (median values: 446 vs. 237 OTUs). Among the rectal samples, the bacterial communities associated with perforated appendicitis were characterized by the highest number of observed OTUs (478 OTUs), compared to non-perforated appendicitis rectal samples (411 OTUs) and rectal samples from subjects with a normal appendix (220 OTUs). This trend was mirrored among the appendix samples. The number of observed OTUs was the highest for the appendix samples from subjects with perforated appendicitis (344 OTUs), appendix samples from patients with non-perforated appendicitis had 228 OTUs. Appendix samples from patients with a normal appendix had 237 OTUs. Based on these observations, severity in diagnosis of appendicitis seems to be characterized by a greater observed bacterial richness (sobs calculator), for both appendix and rectal bacterial communities.

In order to further characterize the bacterial biodiversity of the samples analyzed in this study, richness and diversity estimators were calculated. These ecological indices have classically been used to gain insight about bacterial community structures when using 16S rRNA gene datasets. Community richness, through the use of the Chao1 and ACE estimators, provides information about the estimated number of OTUs present in the samples. Measure of the community diversity, through the use of the Shannon and Simpson indices, provide information about the composition of a given bacterial community, e.g., not only a measure of richness but also take into account the relative abundance of OTUs (or evenness). The Chao1 and ACE richness estimators confirmed the observations previously made using the sobs calculator: sample richness was higher for rectal samples compared to appendix and for perforated appendicitis rectal and appendix samples compared to normal rectal and appendix samples (Table 1). The Shannon diversity index displayed a similar trend with rectal samples displaying a higher diversity compared to appendix samples and with diversity being the highest for increasing severity of appendicitis diagnosis, for both rectal and appendix samples (Table 1). However, the Simpson diversity index showed an opposite trend.

The similarity in microbial composition among the samples analyzed in the present study was further compared using the Bray-Curtis algorithm (Bray, J R et al., *Ecol. Monogr.* 27: 325-349, 1957; Field, J G et al., *Mar. Ecol. Prog. Ser.* 8: 37-52, 1982), which provides an abundance-weighted measure of how similar two communities are in terms of their taxonomic composition. Communities were clustered using an average-linkage algorithm and the results are presented in the cluster dendogram in FIG. 1. Out of the 36 samples analyzed (16 rectal samples and 20 appendix samples), 13 appendix samples clustered together. The appendix cluster was composed almost entirely (12 samples out of 13 samples belonging to that cluster) of samples from patients with appendicitis, both non-perforated and perforated appendicitis, suggesting that the appendix microbiota associated with appendicitis differs from the normal appendix. A second group of 10 samples, composed entirely of rectal samples, clustered separately. For the rectal sample cluster, 8 samples out of 10 samples belonging to that cluster were from appendicitis samples, from patients with both non-perforated and perforated appendicitis, suggesting that an alteration in the appendix microbiota of patients with appendicitis is reflected in an corresponding alteration in the microbiota of the rectum. There was only one pair of rectal-appendix samples from the same subject, who did not have appendicitis (subject 10) that clustered together. None of the other paired appendix and rectal samples from other patients clustered together, reinforcing the observation that the appendix and rectal microbiota have significant differences.

Taxonomic assignments of the 16S sequences revealed 290 different bacterial taxa across all the samples (Tables 2-5). The Metastats program was used for detection of differentially abundant taxa between the appendix and rectal sites, between the appendix of patients with and without appendicitis and between the rectum of patients with and without appendicitis. In patients without appendicitis, three taxa exhibited a statistically significant increased presence in the normal appendix compared to corresponding rectal samples: *Fusibacter* (p=0.009), *Selenomonas* (p=0.026) and *Peptostreptococcus* (0.049). Conversely, in patients without appendicitis, seven taxa exhibited a statistically significant increase in abundance in the rectum compared to corresponding appendix samples: *Frankineae* (p=0.019), *Dyadobacter* (p=0.019), *Actinomycineae* (p=0.033), *Curvibacter* (p=0.042), *Melissococcus* (p=0.042), *Variovorax* (p=0.042) and *Larkinella* (p=0.042) (Table 2).

TABLE 2

Bacterial Genera with Significantly Different Abundance in the Normal Appendix vs. Normal Rectum

| Bacteria | Rectum | Appendix | P-value |
| --- | --- | --- | --- |
| *Fusibacter | 0 | 0.12% +/− 0.07% | 0.009 |
| Frankineae | 0.008% +/− 0.008% | 0 | 0.019 |
| Dyadobacter | 0.008% +/− 0.008% | 0 | 0.019 |
| *Selenomas | 0 | 0.03% +/− 0.02% | 0.026 |
| Actinomycineae | 1.66% +/− 0.92% | 0.065 +/− 0.025% | 0.033 |
| Melissococcus | 0.007% +/− 0.007% | 0 | 0.042 |
| Curvibacter | 0.007% +/− 0.007% | 0 | 0.042 |
| Variavorax | 0.007% +/− 0.007% | 0 | 0.042 |
| Larkinella | 0.007% +/− 0.007% | 0 | 0.042 |
| *Peptostreptococcus | 0.016% +/− 0.016% | 0.32% +/− 0.19% | 0.049 |

In comparing patients with and without appendicitis, five taxa showed a statistically significant increase in the normal appendix when compared to diseased appendices: Paenibacillaceae (p=0.005), Acidobacteriaceae GP4 (p=0.018), Pseudonocardinae (p=0.019), Bergeyella (p=0.019) and *Rhizobium* (p=0.045) (Table 3). When comparing normal appendices to diseased samples, twelve taxa with increased abundance in appendicitis were identified: *Peptostreptococcus* (p=0.0003), Bilophila (p=0.0004), *Bulleidia* (p=0.012), Fusobacterium (p=0.018), Parvimonas (p=0.003), Mogibacterium (p=0.012), Aminobacterium (p=0.019), *Proteus* (p=0.028), *Actinomycineae* (p=0.028), Anaerovorax (p=0.041), Anaerofilum (p=0.045), *Porphyromonas* (p=0.010) (Table 3).

TABLE 3

Bacterial Genera with Significantly Different Abundance in the Normal Appendix vs. the Appendix in Appendicitis Patients

| Bacteria | Normal Appendix | Appendicitis | P-value |
| --- | --- | --- | --- |
| Peptostreptococcus | 0.32% +/− 0.19% | 5.07% +/− 1.2% | 0.0003 |
| Bilophila | 0.07% +/− 0.06% | 0.88% +/− 0.21% | 0.0003 |
| Parvimonas | 4.38% +/− 3.61% | 23.9% +/− 5.33% | 0.003 |
| *Paenibacillaceae 1 | 0.03% +/− 0.03% | 0 | 0.005 |
| Porphyromonas | 0.58% +/− 0.43% | 4.56% +/− 1.54 | 0.010 |
| Bulleidia | 0.70% +/− 0.45% | 3.79% +/− 1.21% | 0.012 |
| Mogibacterium | 0.003% +/− 0.002% | 0.04% +/− 0.01% | 0.012 |
| Fusobacterium | 1.04% +/− 0.67% | 3.21% +/− 0.69 | 0.018 |
| *Acidobacteriaceae Gp4 | 0.019% +/− 0.019% | 0 | 0.018 |
| *Pseudocardineae | 0.026% +/− 0.026% | 0.00105% +/− 0.00105% | 0.019 |
| *Bergeyella | 0.0086% +/− 0.0086% | 0.0019% +/− 0.0019% | 0.019 |
| Aminobacterium | 0.004% +/− 0.004% | 0.13% +/− 0.05% | 0.019 |
| Proteus | 0 | 0.015% +/− 0.015% | 0.028 |
| Actinomycineae | 0.060% +/− 0.025% | 1.42% +/− 0.65% | 0.028 |
| Anaerovorax | 0.14% +/− 0.08% | 0.37% +/− 0.08% | 0.042 |
| *Rhizobium | 0.026% +/− 0.026% | 0.0017% +/− 0.0017% | 0.045 |
| Anaerofilum | 0.01% +/− 0.0044% | 0.04% +/− 0.013% | 0.045 |

When comparing the taxa found in rectal samples from patients with and without appendicitis, three taxa were found to be increased in abundance in the rectal samples of those with appendicitis: Bulleidia (p=0.034), Dialister (p=0.003) and Porphyromonas (p=0.026) (Table 4). These taxa overlap with those taxa identified in the appendix, suggesting that there may be a microbial signal evident in rectal samples indicative of appendicitis.

TABLE 4

Bacterial Genera with Significantly Different Abundance in the Rectum of Patients With and Without Perforation.

| Bacteria | Rectum w/o Appendicitis | Rectum w/Appendicitis | P-value |
| --- | --- | --- | --- |
| Bulleidia | 0.0021% +/− 0.0021% | 0.0238% +/− 0.11% | 0.034 |
| Porphyromonas | 0.103% +/− 0.091% | 0.65% +/− 0.23% | 0.026 |
| Dialister | 0.066% +/− 0.037% | 0.77% +/− 0.23% | 0.003 |

Looking more closely at the appendicitis cases, non-perforated and perforated samples were compared to determine whether any flora were over or under-represented in the most severe form of appendicitis, perforated appendicitis. Five genera showed a significant increase in the perforated group: Bulleidia (p=0.005), Fusibacter (p=0.005), Prevotella (p=0.022), Porphyromonas (p=0.032), Dialister (p=0.003) (Table 5). The observation that taxa found to have increased abundance in the most severe form of appendicitis includes taxa that were also found to be increased in abundance in the rectums of appendicitis patients compared to the rectums of patients without appendicitis further strengthens the model that microbial analysis of rectal samples can provide helpful diagnostic insights into disease in the appendix.

TABLE 5

Bacterial Genera with Significantly Different Abundance in the Appendix of Patients With Perforated Appendicitis vs Appendicitis Without Appendicitis.

| Bacteria | Perforated Appendicitis | Appendicitis | P-value |
| --- | --- | --- | --- |
| Bulleidia | 5.72% +/− 1.72% | 0.88% +/− 0.58% | 0.005 |
| Fusibacter | 0.29% +/− 008% | 0.05% +/− 0.04% | 0.005 |
| Prevotella | 7.66% +/− 1.82% | 2.77% +/− 1.53% | 0.022 |
| Porphyromonas | 6.50% +/− 2.32% | 1.65% +/− 0.99% | 0.032 |
| Dialister | 0.97% +/− 0.30% | 0.26% +/− 0.23% | 0.003 |

Figure 2:
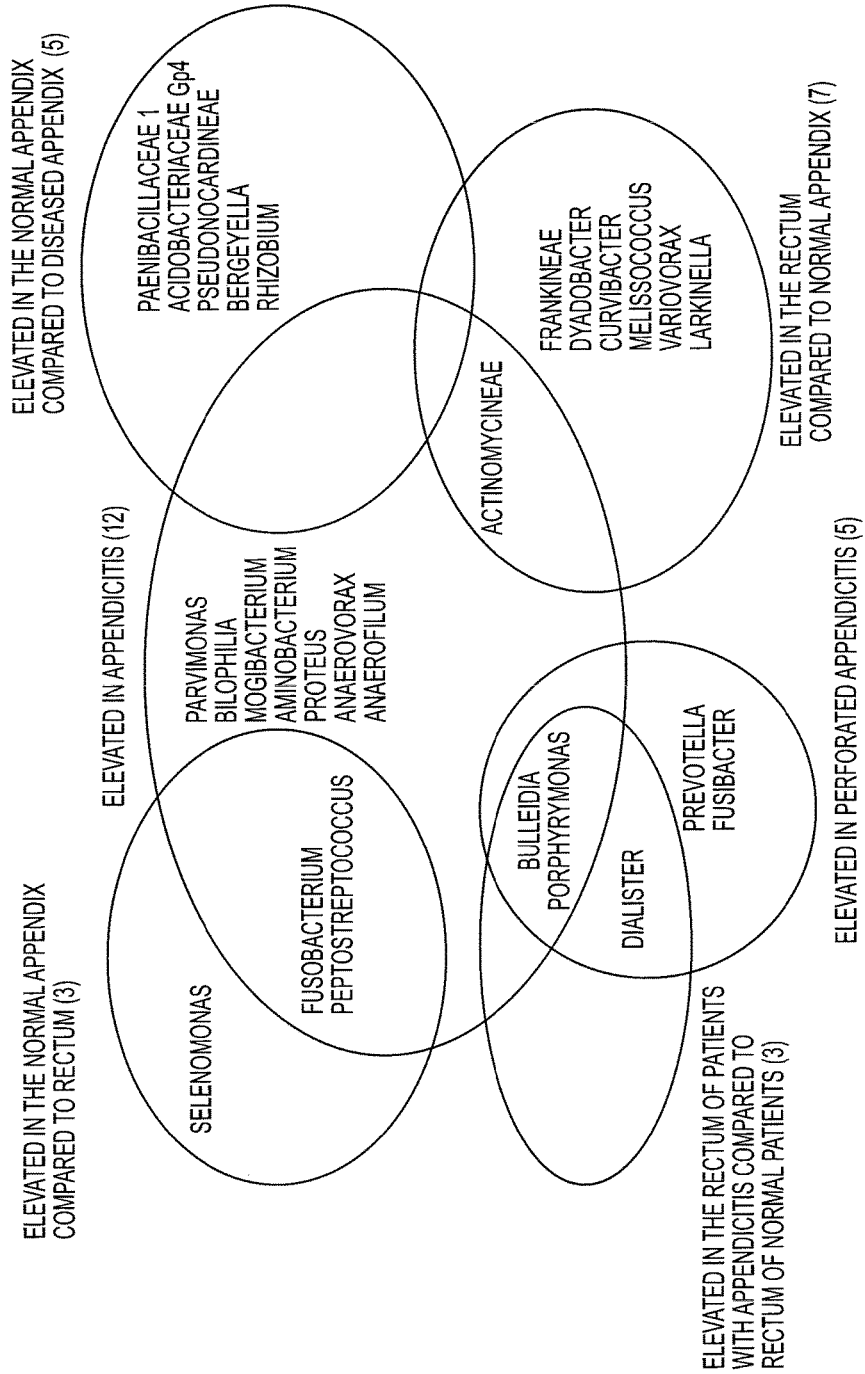
FIG. 2 shows a schematic of identified genera reflecting significant differences comparing the appendix and rectal sites and comparing patients with and without appendicitis. Top row, left to right: bacteria with elevated abundance in the normal appendix compared to the rectum, elevated abundance in appendicitis and elevated abundance in the normal appendix compared to the diseased appendix (appendicitis); Bottom row, left to right: Elevated abundance in the rectum of patients with appendicitis compared to those with normal rectum samples, elevated abundance in perforated appendicitis compared to non-perforated appendicitis and elevated abundance in the normal rectum compared to the normal appendix.

FIG. 2 shows a schematic of the genera showing significant differences comparing the appendix and rectal sites, and comparing patients with and without appendicitis. No significant differences in relative abundance were found across gender, race or age.

Materials and Methods

Ethics Statement. Following approval of the Children's National Medical Center IRB, written consent from the parent or guardian was obtained for collecting appendix and rectal swabs from 21 children undergoing appendectomy.

Study Participants. The ages of participants ranged from 5 months to 18 years (8 males and 13 females) (Table 6).

TABLE 6

Patient Demographics and Clinical Data.

| | |
|---|---|
| Race | African American: 3  Caucasian: 7  Hispanic: 6 |
| | Asian: 2  Other: 2  Not Documented: 11 |
| Age Range | 0-2  3-5  6-10  11-15  16-18 |
| | 1  1  11  6  2 |
| Gender | Male: 8  Female: 13 |
| Most Common Presenting Symptoms | Abdominal pain, nausea, vomiting, anorexia |
| Diagnostic Imaging Used | Computed Tomography: 9 |
| | Ultrasond: 9 |
| | Upper GI: 1 (used to diagnose malrotation that led to incidental appendectomy) |
| | None: 2 (Incidental appendectomy) |
| Appendix Pathology | Normal: 6  Non Perforated: 6  Perforated: 9 |
| Average Length of Stay | 2.8 days (range <24 hrs to 6 days) |

Six patients had normal appendices and fifteen patients had appendicitis, nine of which were categorized as perforated based on pathology report. Seventeen patients underwent an appendectomy with an established or presumed diagnosis of appendicitis. The remaining four patients received an appendectomy incidental to another condition. Incidental appendectomies are common practice in the pediatric population and in some situations considered a standard-of-care to help clarify a diagnosis or eliminate appendicitis from the differential diagnosis in a patient with a history of abdominal complaints or abnormal gastrointestinal anatomy. The most common presenting symptoms for the group of patients with appendicitis were nausea, vomiting, anorexia and abdominal pain. All participants, including patients who underwent incidental appendectomies, were given antibiotics within 24 hours of arrival at the hospital up until the time of surgery. See Table 6 for a list of patient demographics and clinical data.

Sample Acquisition. Once each patient was taken to the operating room and placed under anesthesia, an internal swab of the patient's rectum was performed and stored using the Copan ESwab (Copan Diagnostics) collection and preservation system. After the appendix was resected, it was inspected and opened with Metzenbaum scissors. The full length of the opened appendix was swabbed with an ESwab and the swab was then placed in the transport container. The specimens were stored at −80 C until analysis.

Pathological Diagnosis. The diagnosis of appendicitis was established with pathological reports, which included both macro and microscopic examination of the appendix. Operative reports were reviewed for surgeon commentary on the macroscopic condition of the appendix (e.g., inflamed, injected, grossly perforated, normal).

DNA Extraction and 16S rRNA Gene Sequencing. Total genomic DNA was extracted using a protocol developed at the University of Maryland Institute for Genome Sciences and previously described (Zupancic, M L et al., *PLoS One* 7: e43052, 2012).

Briefly, samples were thawed on ice, incubated in an enzymatic cocktail containing lysozyme, mutanolysin, proteinase K and lysostaphin, after which the microbial cells were lysed using bead beating with the FastPrep instrument (MBio, Santa Ana, Calif.). The DNA was then further extracted and purified using the Zymo Fecal DNA kit (Zymogen).

The variable regions V1-V3 of the 16S rRNA gene were PCR amplified using barcoded 27F and 338R 16S primers, as described previously (Zupancic, M L et al., *PLoS One* 7: e43052, 2012). Negative controls without a template were included for each barcoded primer pair. The presence of PCR amplicons was then confirmed by gel electrophoresis on a 2% agarose gel and staining with ethidium bromide. PCR products were quantified using the Quant-iT PicoGreen dsDNA assay and equimolar amounts (100 ng) of PCR amplicons were pooled prior to pyrosequencing (Zupancic, M L et al., *PLoS One* 7: e43052, 2012). This 16S amplicon pool was sequenced by 454 FLX Titanium sequencing technology using 454 Life Sciences primer A by the Genomics Resource Center at the Institute for Genome Sciences, University of Maryland School of Medicine, using protocols recommended by the manufacturer as amended by the Center. 16S sequence analysis and Statistical Analyses. The pipeline CloVR-16S version 1.1 within the CLoVR system (www.CLoVR.org)(Angiuoli, S V et al., BMC Bioinformatics 12: 356, 2011) was used to bin and trim the sequences. Sequences were binned and trimmed, using the sample-specific barcode sequences and process the resulting sequences for phylogenetic analyses (for more information about the CLoVR-16S workflow, see clovr.org/methods/clovr-16s/). Statistical analysis of differentially abundant bacterial taxa in the 16S rRNA sequence dataset was performed using the METASTATS tool within CLoVR (clovr.org/docs/metastats/). Identified organisms differed significantly (ANOVA, $p<0.05$) in relative abundance by anatomic location (appendix vs. rectum), disease state (appendicitis vs. normal) and disease severity (perforated vs. non-perforated).

What is claimed is:

1. A method for determining the relative abundance of microorganisms corresponding to one or more operational taxonomic units (OTUs) in a test biological sample in a subject, comprising:
    (a) detecting the presence of microorganisms corresponding to one or more operational taxonomic units (OTUs) in a test biological sample obtained from a subject suspected of possibly having appendicitis, wherein at least one OTU is selected from the group consisting of *Bulleidia* and *Dialister;*
    (b) determining the relative abundance of the microorganisms detected in step (a); and
    (c) comparing the relative abundance of the microorganisms in each of the one or more OTUs to a corresponding reference value assigned to each of the one or more OTUs that is representative of a subject that does not have appendicitis,
   wherein the test biological sample is a rectal swab sample,
   wherein step (a) comprises amplifying a marker gene from microorganisms in the one or more OTUs, and
   wherein a significant difference in the relative abundance of *Bulleidia* and/or *Dialister* is detected in the test biological sample as compared to the corresponding reference value or values which significant difference indicates a high risk of appendicitis in the subject.

2. The method of claim 1, wherein step (b) further comprises the sub-step of isolating genomic DNA from microorganisms in the test biological sample.

3. The method of claim 1, wherein the marker gene is selected from the group consisting of 16S rRNA gene, rpoB gene; gyrB gene; gyrA gene; tmRNA gene; recA gene; EF-Tu (tuf) gene; groEL (cnp60, hsp60) gene; atpD gene; ompAgene; gap A gene; pgi gene; fusA gene; ileS gene; lepA gene; leuS gene; pyrG gene; recG gene; rplB gene; pmoA/amoA gene; moX gene; nifH gene; nirS gene; nirK gene; norB gene; mcrA gene and rbcL gene.

4. The method of claim 3, wherein the marker gene is 16s RNA gene.

5. The method of claim 1, further comprising the step of: (d) performing a CT scan or ultrasonography.

6. The method of claim 5, further comprising the step of: (e) treating the subject by administering an antibiotic to the subject and/or surgically removing the appendix from the subject.

* * * * *